(12) United States Patent
Brown et al.

(10) Patent No.: US 7,070,622 B1
(45) Date of Patent: Jul. 4, 2006

(54) PROSTHESIS HAVING A MODULAR SOFT TISSUE FIXATION MECHANISM

(75) Inventors: David R Brown, Warsaw, IN (US); Christina Lakin, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 150 days.

(21) Appl. No.: 10/357,815

(22) Filed: Feb. 4, 2003

Related U.S. Application Data

(63) Continuation-in-part of application No. 10/189,639, filed on Jul. 3, 2002.

(51) Int. Cl.
*A61F 2/38* (2006.01)

(52) U.S. Cl. ............................ 623/20.14; 623/20.21; 623/20.15

(58) Field of Classification Search ... 623/20.14–20.36
See application file for complete search history.

(56) References Cited

U.S. PATENT DOCUMENTS

| 2,719,522 | A | | 10/1955 | Hudack |
|---|---|---|---|---|
| 3,803,641 | A | | 4/1974 | Golyakhovsky |
| 3,859,669 | A | | 1/1975 | Shersher |
| 3,979,778 | A | | 9/1976 | Stroot |
| 4,045,825 | A | | 9/1977 | Stroot |
| 4,045,826 | A | | 9/1977 | Stroot |
| 4,714,475 | A | * | 12/1987 | Grundei et al. .......... 623/20.32 |
| 5,194,066 | A | * | 3/1993 | Van Zile ................ 623/20.15 |
| 5,282,867 | A | * | 2/1994 | Mikhail ................ 623/13.12 |
| 5,314,479 | A | | 5/1994 | Rockwood et al. |
| 5,330,531 | A | | 7/1994 | Capanna |
| 5,358,526 | A | | 10/1994 | Tornier |
| 5,702,486 | A | | 12/1997 | Craig et al. |
| 6,126,695 | A | | 10/2000 | Semlitsch |
| 6,127,596 | A | * | 10/2000 | Brown et al. ............ 623/16.11 |
| 6,165,223 | A | * | 12/2000 | Metzger et al. .......... 623/20.27 |
| 6,264,699 | B1 | * | 7/2001 | Noiles et al. ............ 623/23.23 |
| 6,283,999 | B1 | | 9/2001 | Rockwood, Jr. |
| 6,398,812 | B1 | | 6/2002 | Masini |
| 6,520,994 | B1 | | 2/2003 | Nogarin |
| 6,558,425 | B1 | | 5/2003 | Rockwood, Jr. |
| 6,592,622 | B1 | * | 7/2003 | Ferguson ................ 623/13.14 |

FOREIGN PATENT DOCUMENTS

FR 2634373 * 7/1988

* cited by examiner

*Primary Examiner*—Pedro Philogene
(74) *Attorney, Agent, or Firm*—Harness, Dickey & Pierce, P.L.C.

(57) ABSTRACT

A knee joint prosthesis used for replacing the articulating knee portion of a femur and a tibia. The knee joint prosthesis includes a femoral component, a tibial component, a bearing member, and a soft tissue fixation mechanism. The tibial component includes a tibial bearing surface and an attachment mechanism which facilitates the coupling of the soft tissue attachment mechanism to the tibial component. The soft tissue attachment mechanism has an attachment mechanism which is operable to prevent movement of the soft tissue attachment mechanism with respect to the body. Further, the soft tissue attachment mechanism defines structures which facilitate the coupling of soft tissue to the knee joint prosthesis.

24 Claims, 14 Drawing Sheets

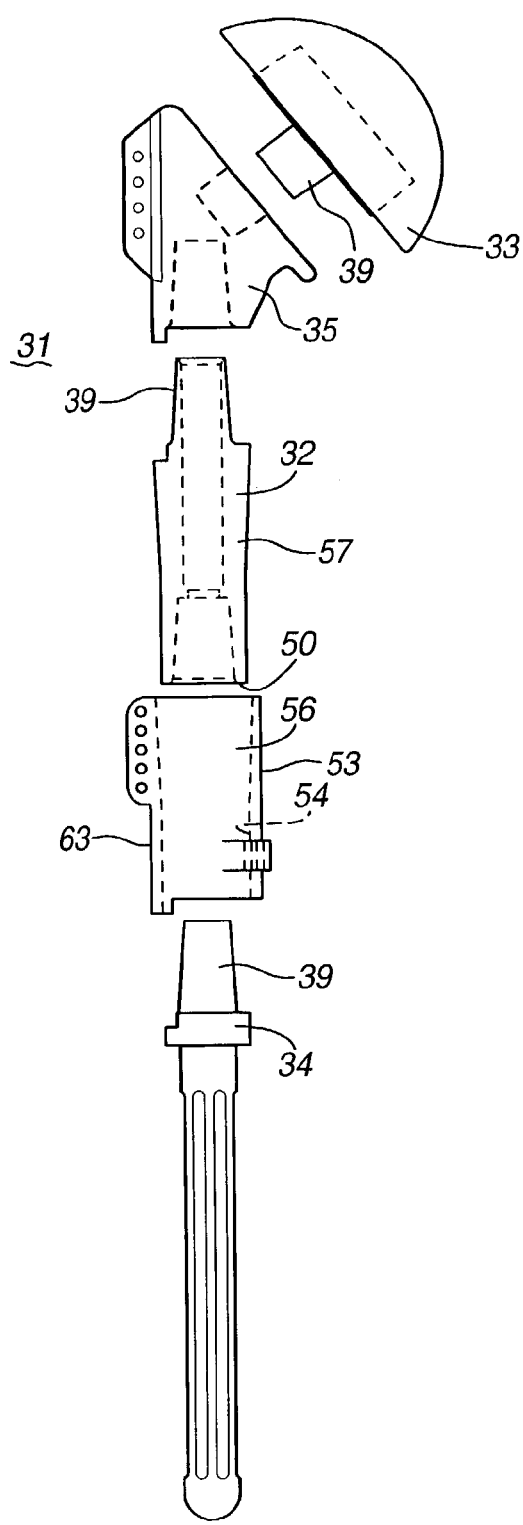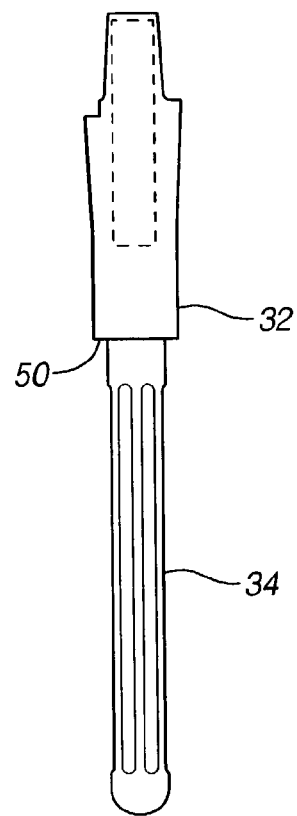
FIGURE 1
FIGURE 2B

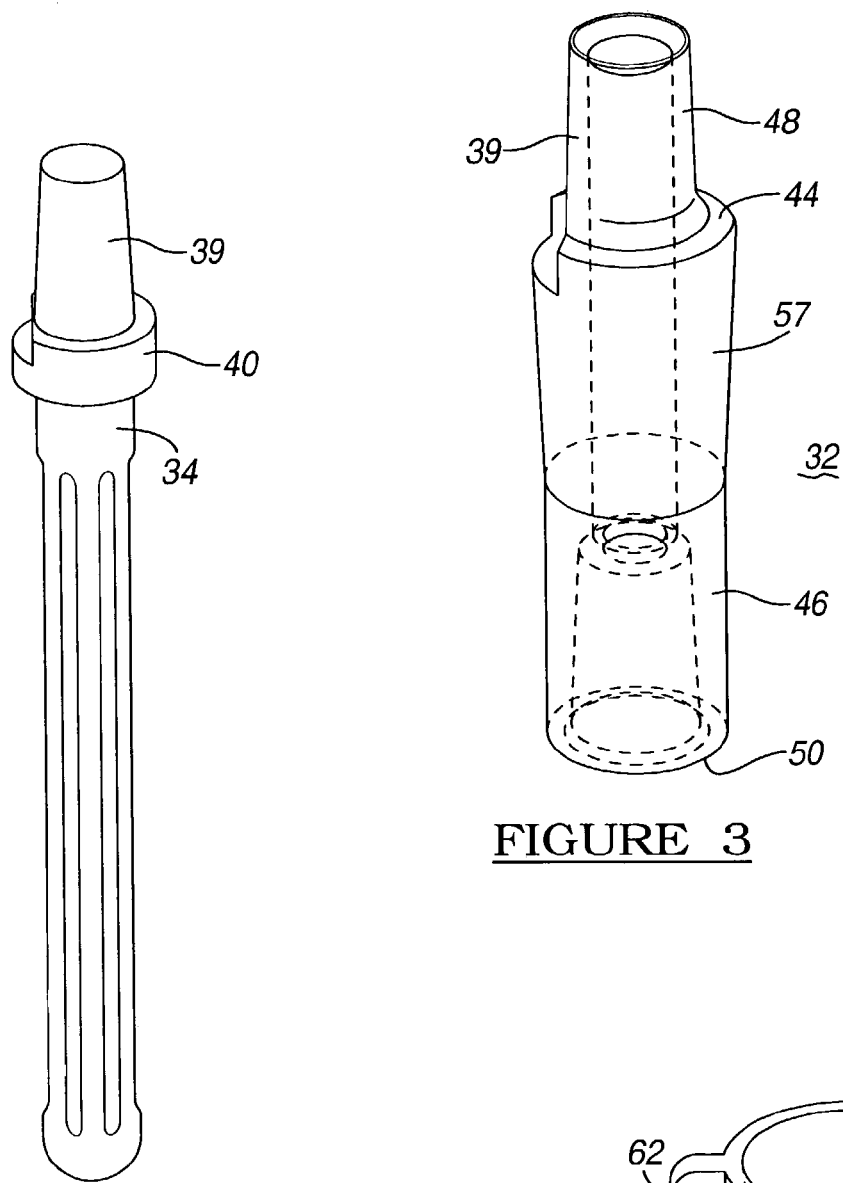
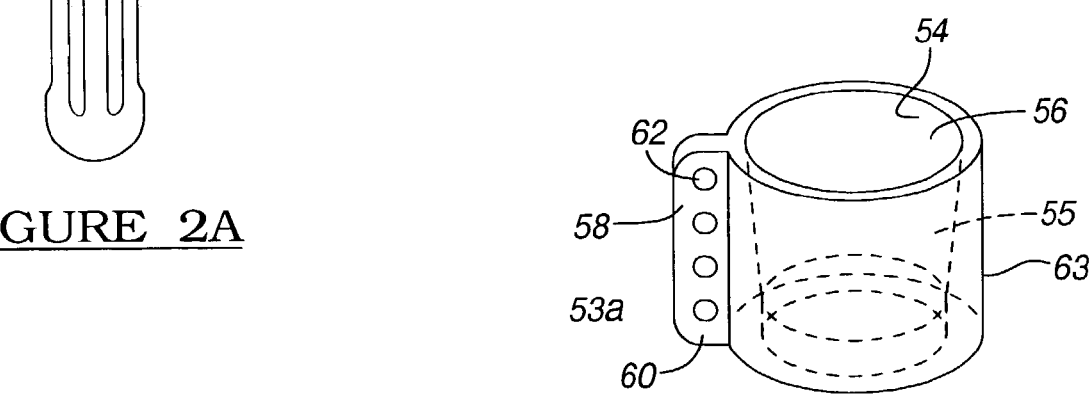
FIGURE 2A

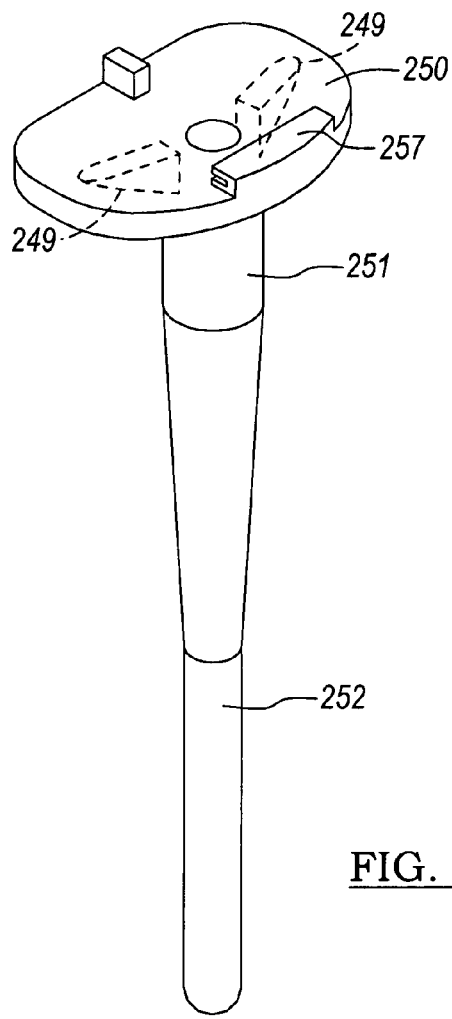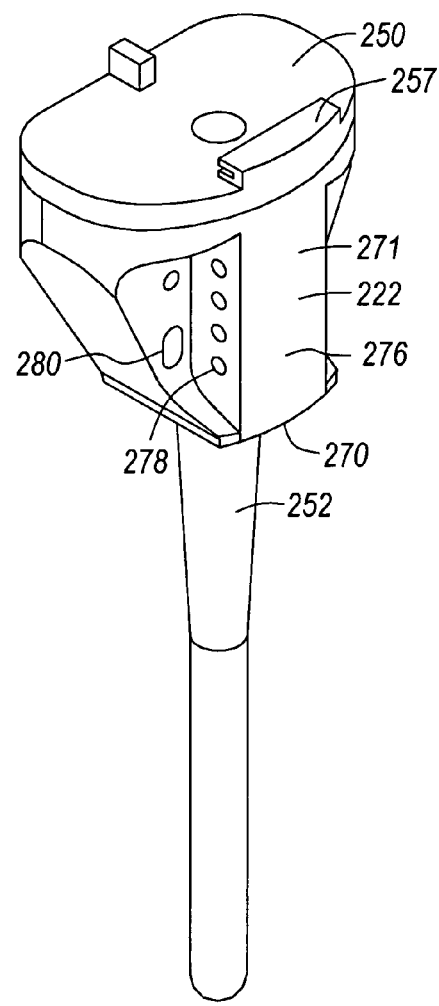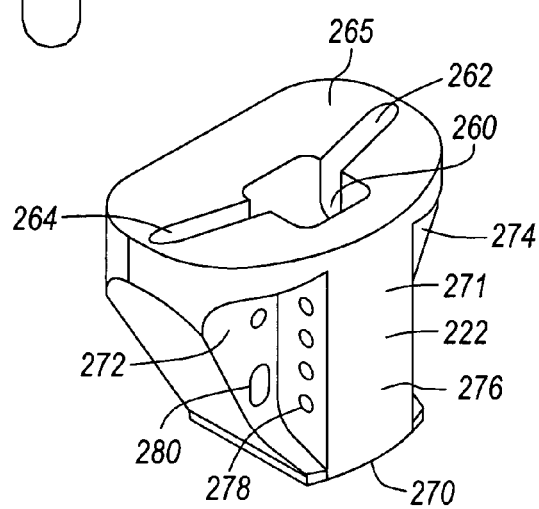
FIG. 19
FIG. 18
FIG. 20

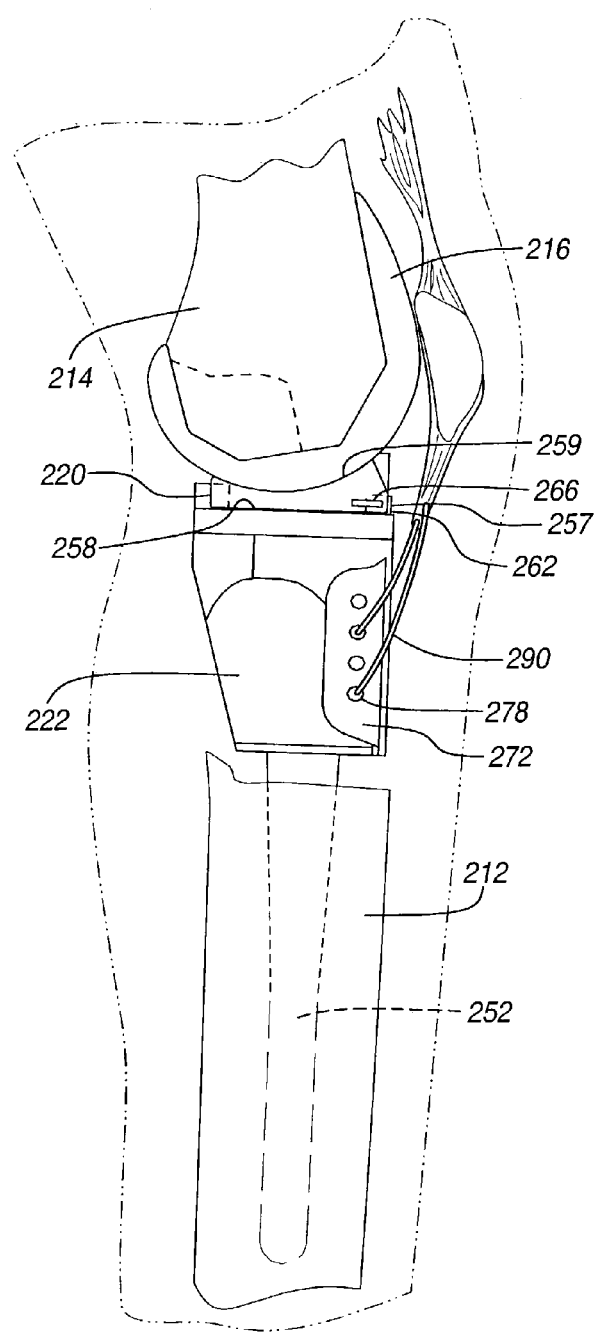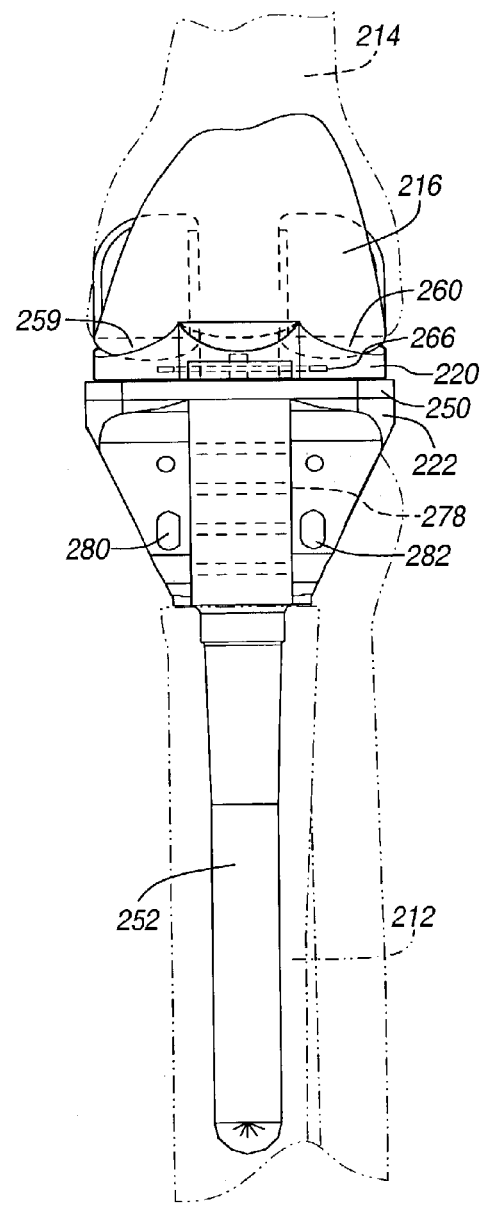
FIGURE 32                    FIGURE 31

PROSTHESIS HAVING A MODULAR SOFT TISSUE FIXATION MECHANISM

CROSS REFERENCE TO RELATED APPLICATIONS

This application is a continuation-in-part application of U.S. patent application Ser. No. 10/189,639 filed on Jul. 3, 2002. The disclosure of the above application is incorporated herein by reference.

BACKGROUND OF THE INVENTION

1. Field of the Invention

This invention relates generally to a method and apparatus for use in orthopedic surgery and, more particularly, to a method and apparatus for providing a prosthesis having a modular soft tissue coupling mechanism. The soft tissue coupling mechanism is a member configured to be optionally coupled to the implant and includes a fixation flange capable of being coupled to soft tissues.

2. Discussion of the Related Art

It is generally known in the art to provide prostheses that replace or reinforce various portions of bone during an orthopedic surgical procedure. However, the current prior art prostheses along with the associated surgical components and instruments utilized during orthopedic surgery may suffer from many disadvantages.

For example, because the extent of degradation is not always evident until during the surgery; extensive bone resection may be necessary. Additionally, etiologies such as bone tumors or those requiring revision of an implanted joint require significant bone removal which may remove soft tissue fixation sites. In these cases, soft tissue fixation to the prosthesis may or may not be necessary. To provide for soft tissue attachment, some replacement joint components provide an integral flange configured to accept soft tissue attached to a lateral surface of the prosthetic replacement joint head. These fixed fixation flanges, however, may not provide the proper locational adaptivity needed during the orthopedic surgical procedure and leave the surgeon with little or no options as to soft tissue attachment.

An example of an orthopedic transplant is a knee joint prosthesis which typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint.

Motion of a natural knee is kinematically complex. During a relatively broad range of flexion and extension, the articular or bearing surfaces of a natural knee experience rotation, medial and lateral angulation, translation in the sagittal plane, rollback and sliding. Knee joint prostheses, in combination with ligaments and muscles, attempt to duplicate this natural knee motion, as well as absorb and control forces generated during the range of flexion. Depending on the degree of damage or deterioration of the knee tendons and ligaments, however, it may be necessary for a knee joint prosthesis to eliminate one or more of these motions in order to provide adequate stability.

What is needed then is a knee prosthesis and associated surgical components for use in orthopedic surgery which does not suffer from the above-mentioned disadvantages. This in turn, will provide a prosthesis which is stable and secure and increases the overall flexibility for a surgeon to fix soft tissues. It is, therefore, an object of the present invention to provide such a prosthesis and associated surgical components for use in orthopedic surgery.

SUMMARY OF THE INVENTION

In accordance with the teachings of the present invention, an apparatus and method for providing a prosthetic having a modular soft tissue attachment mechanism is disclosed. The apparatus and method employs a modular soft tissue attachment mechanism for use during the orthopedic surgical procedure.

In one embodiment, an orthopedic implant has a body that is at least partially implantable within a bone. A mechanism for coupling soft tissue to the body is provided. The mechanism for coupling soft tissue to the body has an attachment mechanism operable to prevent movement of the coupling mechanism with respect to the body.

In another embodiment, a tibial prosthetic having a tibial tray and a bearing is presented. The tibial prosthetic has a base member defining a fixation surface which is coupled to the bearing. A soft tissue fixation member is provided which has a coupling mechanism, that functions to couple the soft tissue fixation member to the tibial prosthetic. A locking mechanism is provided which prevents movement of the soft tissue fixation member with respect to the base member.

In another embodiment, a modular replacement knee joint component is used for joint arthroplasty such that a replacement joint component is adapted to be implanted into a bone and engaged by a femoral portion of the replacement joint component. The replacement joint component includes a semi lunar bearing surface having a first articulating surface and a second medial surface, which is opposite to the first articulating surface. The first articulating surface is adapted to engage the articulating surface of a femoral portion and the second medial surface is adapted to engage a fixation component. The fixation component has a first surface adapted to be secured to the second medial surface and a second surface adapted to be accepted into an intermedullary canal of a tibia. The second surface extends from the second medial surface such that the base member provides a fixation surface. A soft tissue fixation member, is coupled to the replacement joint component. The soft tissue fixation member has an exterior flange having a soft tissue coupling member.

A method for implanting an knee prosthetic is further disclosed. The method includes selecting an appropriately sized prosthetic component. Next, a determination is made if soft tissue fixation to the implant is necessary. Should it be necessary to couple soft tissue to the implant, a soft tissue fixation mechanism is attached to the implant. The implant is subsequently implanted.

Use of the present invention provides an apparatus and method for providing a prosthetic having a modular soft tissue attachment mechanism for use during an orthopedic surgical procedure. As a result, the aforementioned disadvantages associated with the currently available prostheses and associated surgical components have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is an exploded view of the prosthetic component according to the teachings of the preferred embodiment;

FIGS. 2a–2b are views of a bone fixation member of humeral component of FIG. 1;

FIG. 3 represents a base member according to the teachings of the present invention;

FIGS. 4–8 are alternate embodiments for a soft tissue fixation member of the humeral component of the present invention;

FIG. 18 depicts a tibial component of the knee prosthesis of FIG. 17;

FIG. 19 depicts a tibial tray component of the tibia component shown in FIG. 18;

FIG. 20 depicts a soft tissue fixation mechanism as used in FIG. 18;

FIGS. 31 and 32 represent front and side views of the knee prosthetic being incorporated into a knee.

DETAILED DESCRIPTION OF THE PREFERRED EMBODIMENTS

The following description of the preferred embodiments concerning an apparatus and method for providing a prosthesis having a modular soft tissue attachment mechanism is merely exemplary in nature and is in no way intended to limit the invention, its application, or uses. Moreover, while the present invention is discussed in detail in relation to a shoulder joint, a hip joint, and a knee joint replacement, the present invention is not limited to only these procedures. For example, any type of orthopedic surgical procedure that replaces or reinforces bone may employ the present invention.

Figure 9:
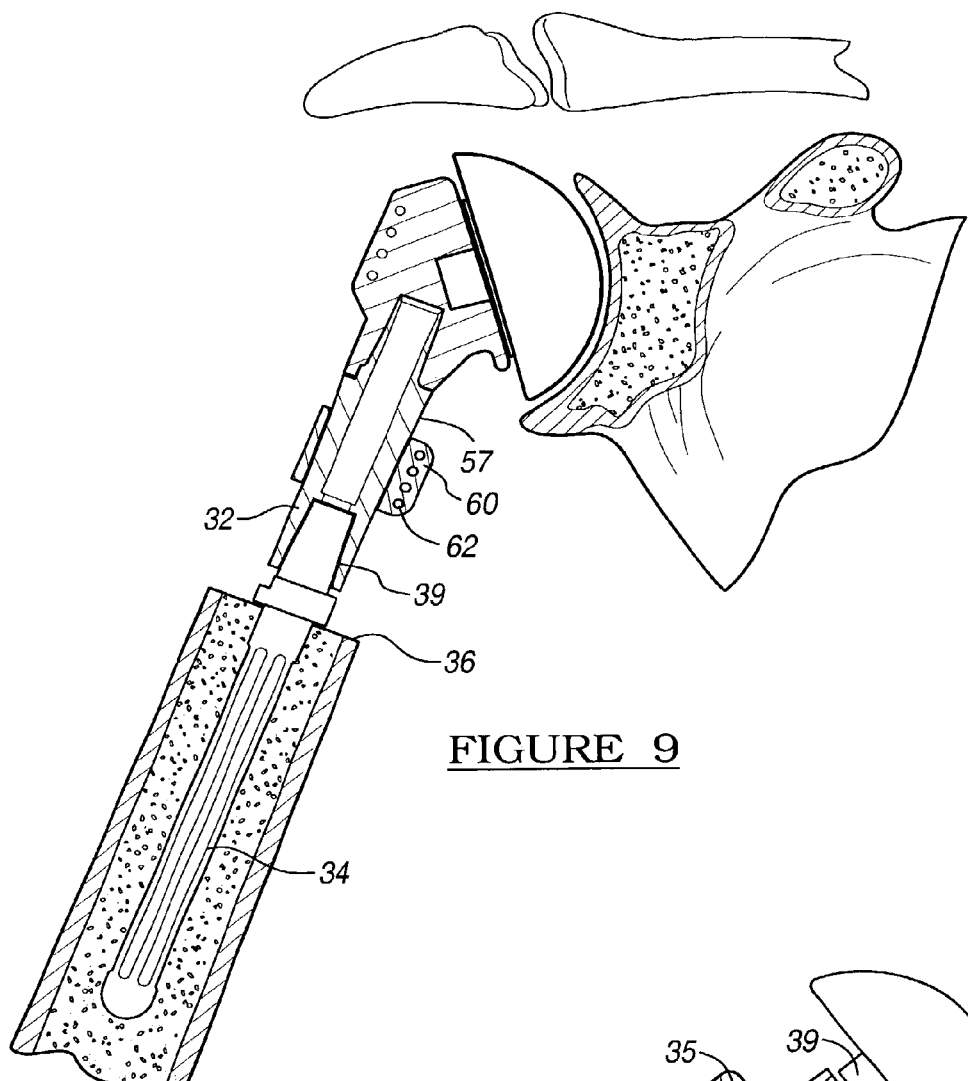
FIG. 9 represents the prosthetic according to the present invention implanted within a skeletal structure.

FIG. 1 depicts components used in a shoulder arthroplasty of the current invention. As shown, a modular humeral component 31 has a base member 32 and a head member 33. The base member 32 is configured to be coupled to a fixation stem 34 which is used to attach the humeral component 31 to a resected bone 36 of the humerus 38 by way of a Morse type taper 39 or any other attachment mechanism (see FIG. 9). If a total shoulder arthroplasty is performed, a glenoid component 40, shown in FIG. 9, is first implanted into the scapula 42 using techniques well known in the art. The glenoid component 40 is preferably of the type disclosed in U.S. Pat. No. 5,800,551, which is hereby incorporated by reference, or any other suitable conventional glenoid component. The humeral component 31 is designed to allow rotational and transitional movement of the head member 33 with respect to the glenoid component 40.

FIG. 1, shows a humeral head 33 which mates through a humeral body component 35 to the base member 32 by way of a Morse type taper 39 or any other appropriate attachment mechanism. It should be noted that a surgical kit of the components would contain numerous head members 33, each having a varied radius of curvature, diameter, and height to allow a surgeon to optimize joint movement. Additionally, a surgical kit would contain the instruments needed for implantation (described later).

FIGS. 2a and 2b depict fixation stems 34 according to the teachings of the present invention. FIG. 2a discloses a conventional fixation stem which will be mounted to the base member 32 via a Morse type taper 39. The Morse type taper 39 is disposed upon a shelf member 40 which functions as an interface surface to a resected bone (as described below). Alternatively, as depicted in FIG. 2b, the fixation stem 34 can be integral to the base member 32. Particularly, the stem 34 is disposed perpendicularly to the surface 50 of the base member 32. In this configuration, however, the surface 50 must be configured so as to allow the interior bore 56 of the soft tissue fixation mechanism 53 to be disposed about the base member 32.

FIG. 3 depicts the base member 32 of one embodiment of the current invention. The base member 32 is defined by a shelf member 44, which may function as an impaction surface. The shelf member 44 can have at least one mating member 48 for engaging the humeral body component 31. It is preferred that the mating member 48 be a defined Morse type taper 39 or other suitable attaching mechanism. In addition to the mating member 48, each base member 32 has or is coupled to a fixation stem 34 disposed on the lower lateral surface 50. The fixation stem 34 is generally perpendicular to the lower lateral surface 50, and can be a male or female Morse type taper. A cylindrical outer surface 46 of the base member 32 is defined between the shelf member 44 and the flat lower lateral surface 50. Optionally, disposed about the base member 32 is soft tissue fixation mechanism 53. Soft tissue fixation mechanism 53 is a cylindrical tube having an inner surface 54, which defines the inner bore 56 and an exterior surface 63.

The humeral body component 31, stem 34, base member 32, and soft tissue fixation mechanism 53 is made of bio-compatible materials such as, without limitation, titanium, titanium alloys, surgical alloys, stainless steels, biocompatible ceramics, and cobalt alloys. Optionally, the base member 32 can additionally be made of materials such as biocompatible ceramics and resorbable and non-resorbable polymers and other anticipated bio-compatible metallic or polymeric materials. Should the base member 32 be made of non-metallic components, a fastener may be needed to couple the body 31 to the base member 32. Additionally, the fixation mechanism 53 can be an allograft material.

As best seen in FIGS. 4–8, the soft tissue fixation mechanisms 53a–e are configured to be annularly disposed about the cylindrical outer surface 46 of the base member 32. The inner surface 54 is configured to have an attachment mechanism 55 disposed thereon. Optionally, this attachment mechanism 55 can take the form of a 60 included Morse type taper which couples to a Morse type taper 57 defined on the cylindrical outer surface 46 of the base member. The exterior surface 63 of the soft tissue fixation mechanism 53*a*–*f* define soft tissue fixation members 58. As best seen in FIG. 4, the soft tissue fixation members 58 can take the form of a longitudinal flange 60. The longitudinal flange 60 defines through suture bores 62 which function as sites for coupling soft tissue to the prosthetic. Alternately, the soft tissue fixation members 58 can take the form of multi-directional flanges 64 or as an attachable suture anchor attachment site. The use of a Morse type taper 55 to couple the soft tissue fixation member 58 to the base member 32 allows a physician to rotate at any desired location the location of the fixation flanges.

FIGS. 4–8 depict alternate embodiments of soft tissue fixation mechanism 53*a*–53*e*. In this embodiment, the soft tissue fixation mechanisms 53*a*–53*e* are cylindrical members which define an interior bore 56. The interior bore 56 defines an attachment mechanism 58. Additionally, depending on the length of the soft tissue fixation mechanism 53*a*–*e*, a through suture bore 62 can be defined. The attachment mechanism 55 is a female portion of a 6° Morse type taper. The 6° included Morse type taper couples to the 6° included Morse type taper defined on the exterior surface of base 32. As can be seen in FIGS. 4, 5, 6, and 8, the soft tissue fixation mechanism 53 has an exterior surface 63 which defines at least one soft tissue coupling flange 60. This flange 60 is generally coaxial with the body of the implant and is generally parallel to the implant centerline.

Figure 5:
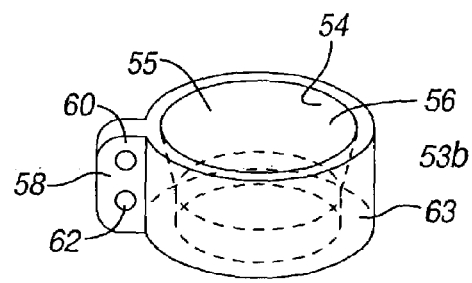
Figure 6:
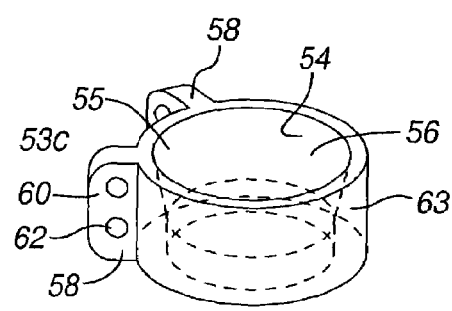
Figure 7:
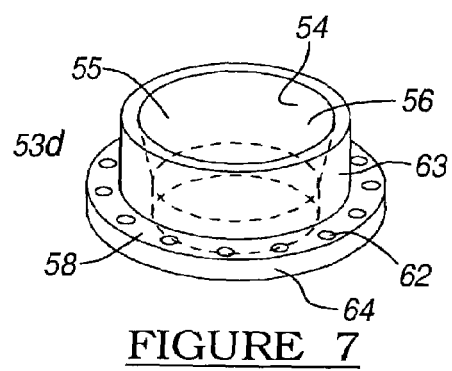
Figure 8:
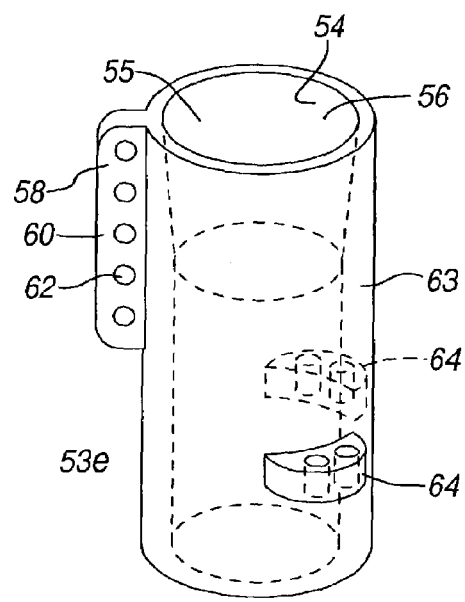

As can be seen in FIGS. 7 and 4, the flange 64 can also be configured so as to define a plane perpendicular to the centerline of the base member 32. Each flange 64 defines at least one through suture bore 62 or slot which is used to couple the soft tissue to the soft tissue fixation mechanism 53*a*–*e*. A plurality of suture bores 62 can be radially disposed about the exterior surface 63, as illustrated in FIG. 7. It should be noted that each soft tissue fixation mechanism 53*a*–53*e* can have a plurality of flanges 64 and 60. While through suture bores 62 are shown for use to couple the soft tissue, those skilled in the art will recognize other structures such as keyed slots and channels and angled flange members can be used to accept sutures and suture anchors. Additionally, wires, aortic graft, and tape can be used to fix the soft tissue.

FIG. 9 discloses the orthopedic implant 31 shown in FIG. 1 disposed within a patient. Shown is the bone fixation stem 34 disposed within the medullary canal of the resected bone 36. The stem 34 is coupled to the base member 32 via a Morse type taper 39. Disposed about the base member 32 is the soft tissue fixation mechanism 53*a*. As can be seen, the mounting flange 60 can be rotated about the base member 32 to fix extensor and abductor soft tissue to the prosthetic 31. In situations where the flexor abductor must be fixed to the prosthetic, a soft tissue attachment mechanism such as the one shown in FIG. 4 can be used.

Figure 10:
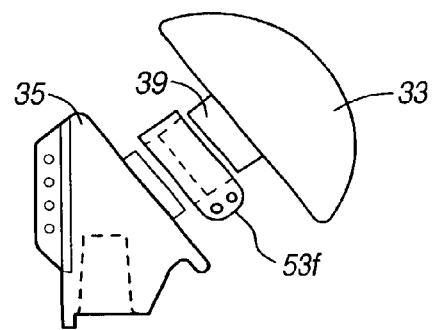
FIG. 10 represents an alternate embodiment of the present invention.

FIG. 10 discloses an alternate view of the present invention. Shown is a soft tissue fixation mechanism 53*f* disposed between a humeral head 33 and a humeral head base 35. As with the soft tissue fixation members depicted in FIGS. 4–8, it is envisioned that the soft tissue fixation mechanism 53*f* can have either longitudinal or transverse mounting flanges.

As shown in FIGS. 11–15, the attachment mechanism 55 need not be a Morse type taper. FIGS. 13*a* and 13*b* show the attachment mechanism 55 being tapered key slots 66 which couple to a locking flange 68 disposed on the base member 32. It is envisioned that as few as one and as many as sixteen tapered key slots 66 can be disposed on the inner surface 54 of the soft tissue fixation member 53. Base members, as disclosed in FIG. 11, would be used in situations where maximum rotational torque may be applied by the soft tissue to the prosthetic. In this regard, while a Morse type taper fixation is usable in a humeral prosthetic, a key/slot configuration may be necessary for a higher rotational stability.

Figure 11:
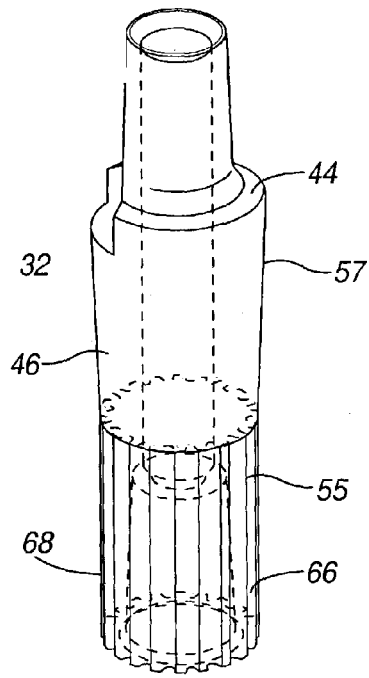
FIG. 11 represents an alternate base member according to the teaching of the present invention.
Figure 12:
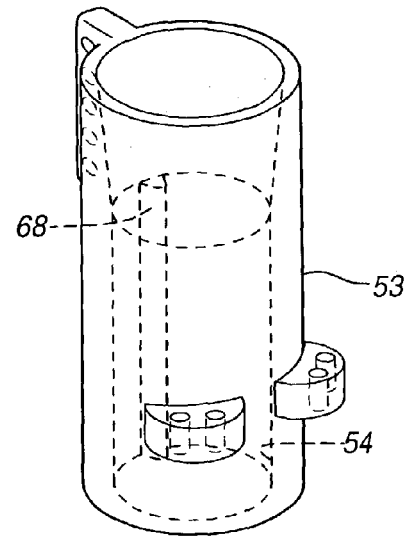
FIG. 12 represents an alternate soft tissue fixation member according to the teaching of the present invention.
Figure 13A:
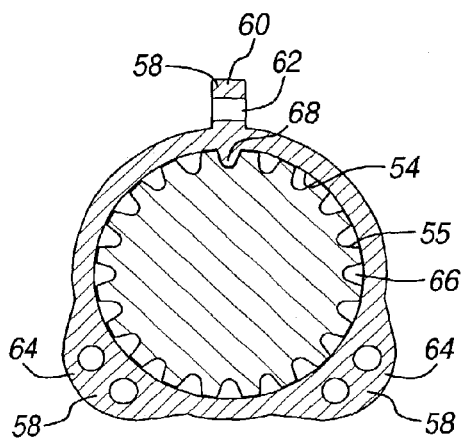
FIGS. 13a–13b represent the interaction of the soft tissue fixation member of FIG. 12 with the base according to FIG. 11.
Figure 13B:
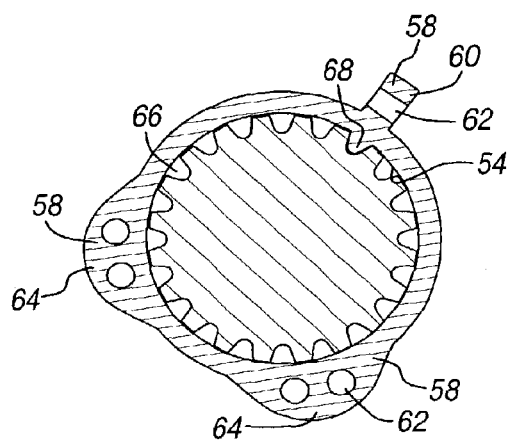

FIG. 11 defines base members 32 having the shelf member 44 and a cylindrical outer surface 46. Additionally shown is a channeled outer surface 68 for mating the base member 32 to the soft tissue fixation members 58. The base members 32 and soft tissue fixation members 58 are depicted in FIGS. 13*a* and 13*b* and are shown mated. As can be seen, locking flange 68 is disposed on the inner surface 54 of the soft tissue fixation member 58. This locking flange 68 is coupled to a channel formed on the exterior surface of the base 32. FIG. 13*b* shows the rotation of the soft tissue fixation members 58 about the base member 32, which allows the physician to regulate or adjust the location of the optional fixation flange.

The method for implanting the humeral component 30, along with associate surgical components utilized will now be described with reference to FIG. 16. The head of the humerus 38 is resected using a saw, then planed flat. With the resected bone 36 of the humerus 38 exposed, an appropriately sized implant is chosen for insertion into the medullary canal of the humerus.

Once the proper sized implant is chosen, the resected bone 36 of humerus 38 is optionally reamed using a reamer shaft with the driver. Upon rotating the surface of the reamer, the resected bone 36 of the humerus 38 is prepared to mate or conform with the shape of the fixation stem 34 of the base member 32.

Once the inside surface of the resected bone 36 of the humerus 38 has been prepared, the stem 34 can be inserted into the medullary canal. Prior to insertion, a decision is made whether soft tissue fixation to the implant is necessary. Should it be necessary, a soft tissue fixation mechanism 53 is disposed about the base member 32. The soft tissue fixation mechanism 53 is rotated into position and fixed to the base member 32 in its proper orientation. It is envisioned that fixation stem 34 of the base member 32 can be forced into the medullary canal to displace the bone material. Optionally, the medullary canal can also be reamed to a larger interior diameter to accept the stem 34 without displacement of the bone material.

The modular nature of the humeral component 30 of the present invention allow a set of various types of both replacement base members 32, humeral body components 31, and stems 34 to be formed. In using such a set, a surgeon can interoperatively choose the appropriate base member depending on the patient's particular condition. Additionally, the surgeon can then choose from a set of head members 33, which both have the proper articulating surface radius and a proper coupling to the humeral body component 31.

Figure 14:
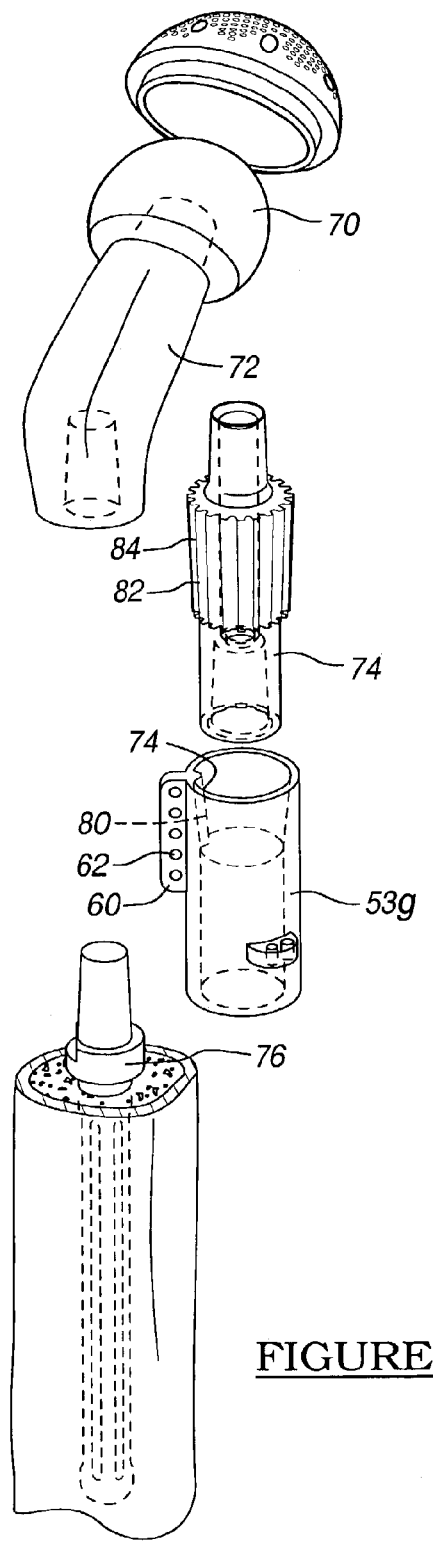
FIGS. 14 and 15 represent the application of the present invention to a femoral implant.
Figure 15:
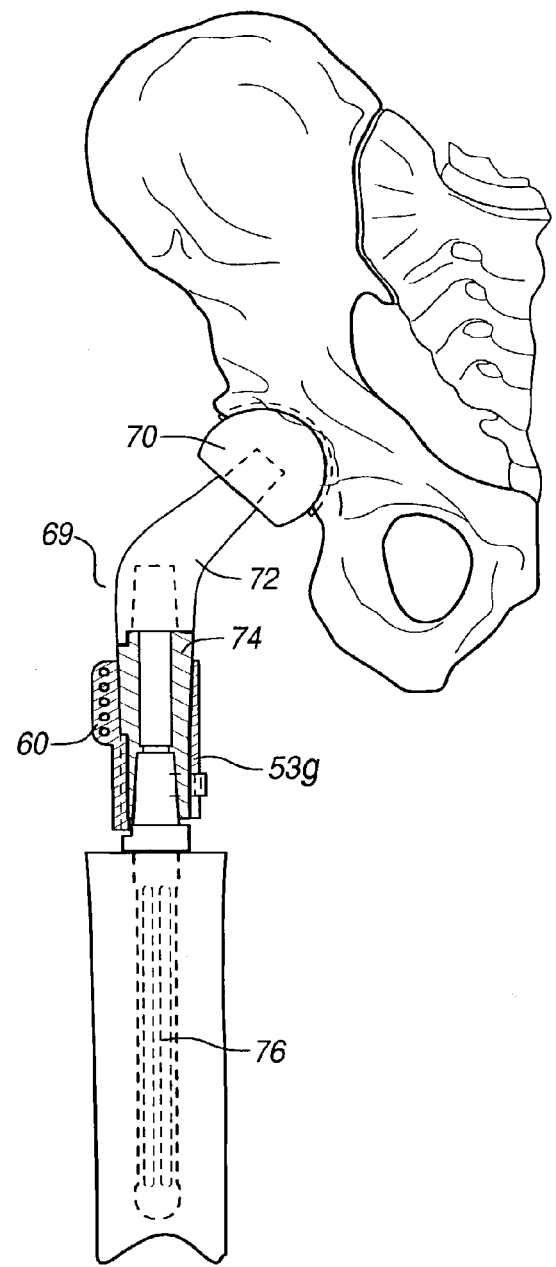

FIGS. 14 and 15 show the soft tissue fixation member according to the present invention used in a hip implant. FIG. 14 depicts an exploded view of an implant having a head portion 70 with a neck 72. Additionally, the prosthetic has base portion 74 and a femoral stem 76. Under normal conditions, the femoral prosthetic 69 can be assembled without the use of a soft tissue fixation mechanism 53*g*. Soft tissue fixation mechanism 53*g* is shown having an interior locking mechanism 78 taking the form of a tapered flange 80. The tapered flange 80 is configured so as to be lockably positioned within a channel 82 disposed on an exterior surface 84 of the base portion 74. As can be seen, the soft tissue fixation mechanism 53*g* is rotatable about the base portion 74, allowing the soft tissue coupling flange 86 to be rotationally positioned in any location about the centerline of the implant.

FIG. 15 depicts the soft tissue fixation mechanism 53g according to the teachings of the present invention disposed about the hip prosthetic. In this configuration, the head 70 is disposed within the acetabulum. The neck 72 is coupled to the base portion 74 and the base portion 74 is coupled to the stem 76 using a standard locking Morse type taper 88.

Figure 16:
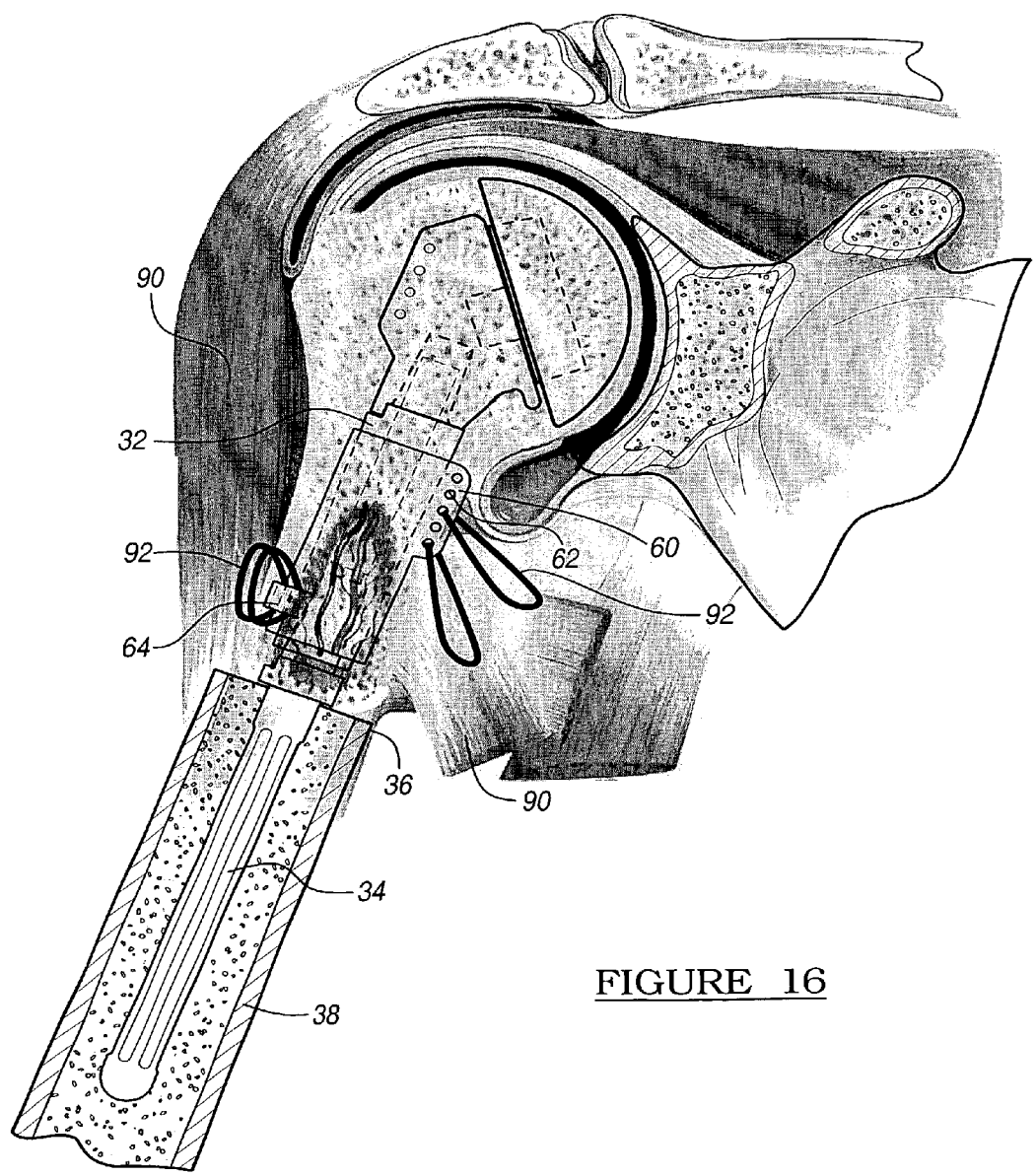
FIG. 16 represents cross-sectional views of implanted humeral components of the present invention and its fixation to soft tissue.

FIG. 16 depicts the coupling of soft tissue to varying flanges 60 and 64 of the prosthetic. Generally, the implant will be implanted into the medullary canal of the resected bone 36 prior to the coupling of the soft tissue 90 to the soft tissue fixation mechanism 53a. As can be seen, the soft tissue 90 is coupled to the soft tissue attachment mechanism via standard sutures 92 or suture anchors, while the attachment mechanism can take the form of a threaded fastener or appropriate adhesive.

Figure 17:
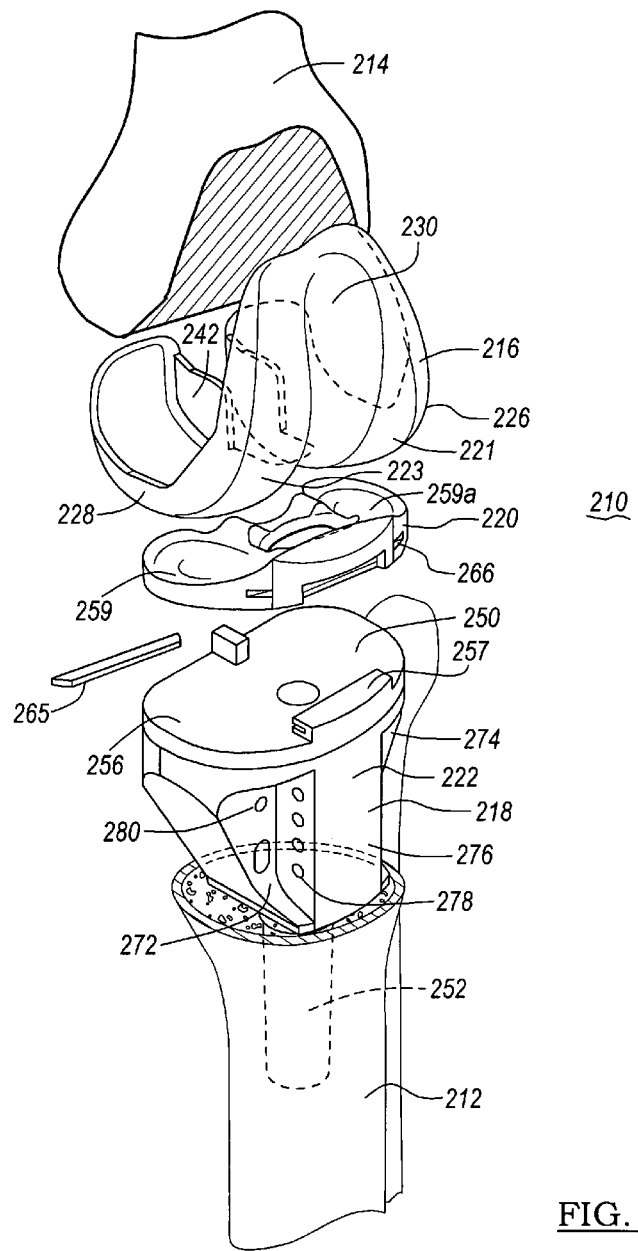
FIG. 17 depicts a prosthesis according to the teachings of the present invention.
Figure 23:
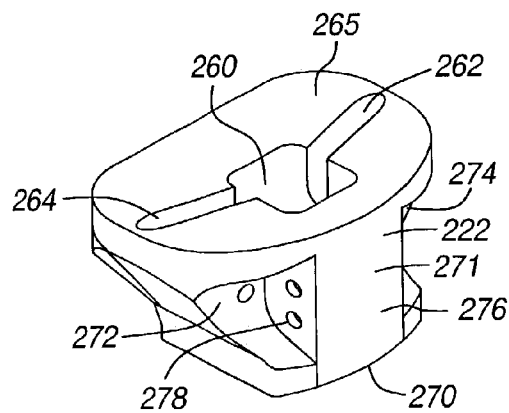
FIGS. 21–23 depict tibial components according to another embodiment of the invention.
Figure 22:
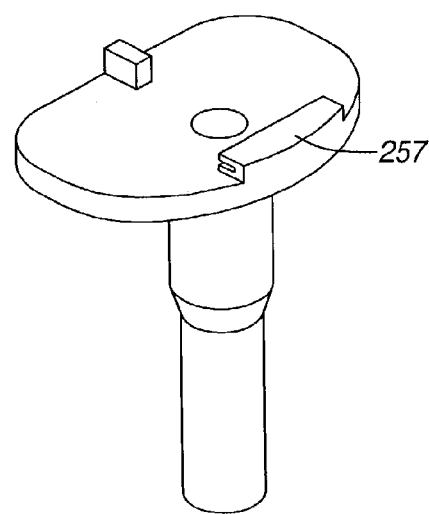

Referring to FIGS. 17–29, there is shown a knee joint prosthesis 210 according to the teachings of a first embodiment of the present invention. The knee joint prosthesis 210 is generally known as a fixed bearing knee joint prosthesis 210 which is designed to provide adequate stability in case of moderate deterioration or instability of the human knee. This most typically occurs when the anterior and posterior cruciate ligaments are sacrificed or dysfunctional and the medial and lateral collateral ligaments remain functionally intact. The knee joint prosthesis 210 is shown in FIGS. 17 and 23 as being secured to a tibia 212 and a femur 214 of a surgically resected left knee joint. The knee joint prosthesis 210 includes a femoral component 216, a tibial component 218, a fixed tibial bearing 220, and a soft tissue fixation mechanism 222.

Referring briefly to FIG. 17, the femoral component 216 is adapted to be secured to a distal end of the femur 214 and includes a first condylar portion 221 and a second condylar portion 223 that provide a first femoral bearing surface 226 and a second femoral bearing surface 228, respectively. The first and second condylar portions 221 and 223 of the femoral component 216 are interconnected by an intercondylar portion 230 that defines an intercondylar recess 232. The intercondylar portion 230 includes an intercondylar coupling mechanism such as a box 242 that defines the intercondylar recess 232 as is known in the art.

The tibial component 218 is adapted to be secured to the proximal end of the tibial 212 after the tibia has been resected in a manner known in the art. The tibial component 218 includes a substantially planar platform-like tibial tray 250 and an inferiorly extending tibial stem 252. The tibial stem 252 is adapted to be received in a corresponding opening made by the surgeon in the longitudinal center of the tibia 212. The tibial tray 250 defines a fixation mechanism 257 configured to be fixably coupled to the fixed bearing 220 of the tibial tray 250. The tibial tray or plateau 250 and stem 252 are preferably manufactured from cobalt-chromium-molybdenum or any other suitable biocompatible material. The top of the tibial tray 250 may be highly polished to provide a substantially smooth tibial bearing surface 256. As shown in the previous prosthesis, an attachment mechanism 251 is provided to couple the tibial tray 250 to the soft tissue fixation mechanism 222. The attachment mechanism 251 can take the form of a generally cylindrical surface and further can take the form of a Morse type taper, a keyed slot, a tapered flange, a plurality of channels, a threaded fastener, and polymer bone cement.

Figure 21:
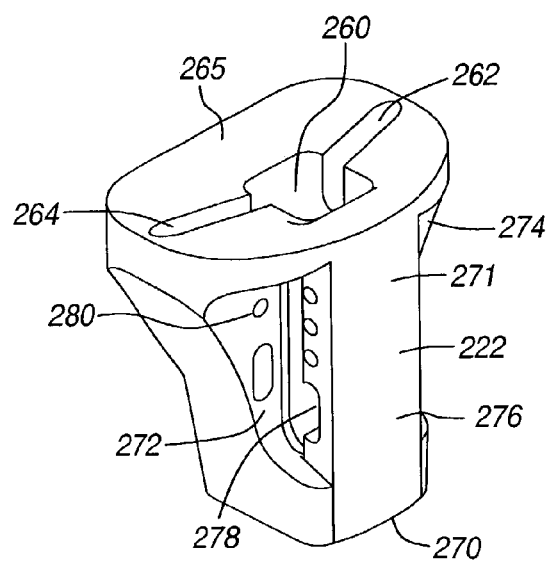

FIGS. 20, 21, and 23 illustrate versions of the soft tissue fixation mechanism 222. The soft tissue fixation mechanism 222 defines a central through bore 260, which is adapted to annularly engage and accept the tibial stem 252. The soft tissue fixation mechanism 222 further defines a pair of angular slots 262 and 264 on a proximal surface 265 of the soft tissue fixation mechanism 222, which are configured to engage a pair of inferior extending corresponding flanges 249 disposed on the tibial tray 250, as shown in phantom lines in FIG. 19. The flanges function to prevent rotation of the soft tissue fixation mechanism 222 about the tibial stem 252. The inferior flanges 249 can be tapered.

The soft tissue fixation mechanism 222 has a distal surface 270 which functions as a load bearing interface between the resected tibia and the tibial tray 250. The anterior surface 271 of the soft tissue fixation mechanism 222 defines a pair of cut out regions 272 and 274. These cut out regions form a flange 276 which defines a plurality of first orifices 278 which are configured to accept sutures coupled to the patient's soft tissue. The flange 276 can be either perpendicular, angled, or parallel with an axis defining the tibial stem 252. In this regard, the first orifices 278 are configured to be coupled to the ligamentum patella. Further defined within the cut out regions 272 and 274 are a second and third set of orifices 280 and 282. The second and third set of orifices 280 and 282 are configured to be coupled to the external and internal lateral ligaments. It is envisioned that clearance within the system, for example a hole disposed through the tibial tray 250, can facilitate the coupling of the anterior or posterior crucial ligaments.

Figure 25:
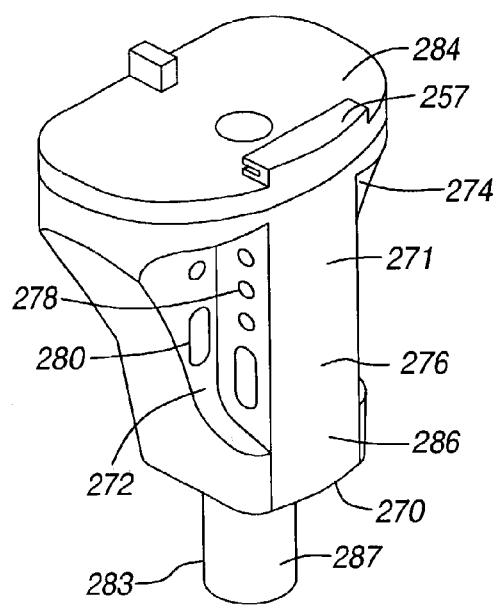
FIGS. 24–26 depict a modular tibial component having an integral soft tissue fixation mechanism.
Figure 26:
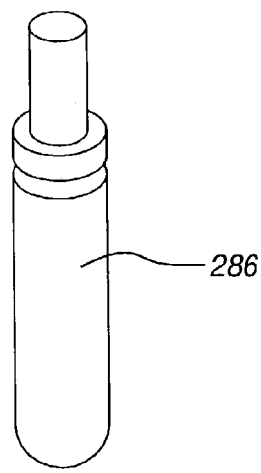
Figure 24:
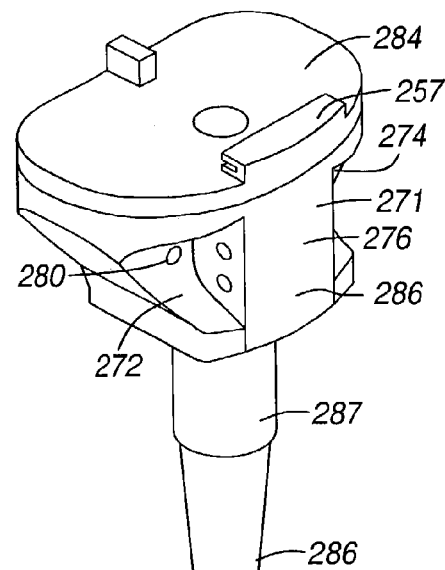
Figure 28:
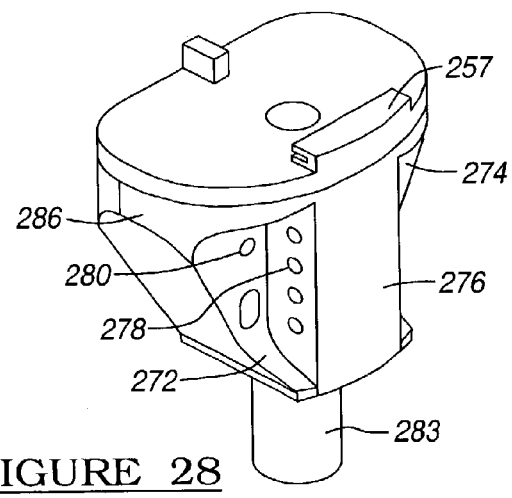

FIGS. 25 and 28 represent tibial trays 284 which have an inferiorly extending stem fixation mechanism 283, and an integral or modular stem 286. The tibial trays 284 are shown having a first thickness in the inferior direction which corresponds to the amount of tibial bone mass which must be resected. As seen in FIGS. 24 and 25, the depth of the tibial tray can be increased should additional bone need be resected from the patient. As can be seen, the integral soft tissue fixation mechanism can define a stem coupling mechanism 287 which can facilitate the coupling of stems having various lengths. The soft tissue mechanism may be porous coated to promote adhesion of tissue in growth. Longer soft tissue fixation mechanisms are envisioned being used with higher constraint tibial implants.

Figure 27:
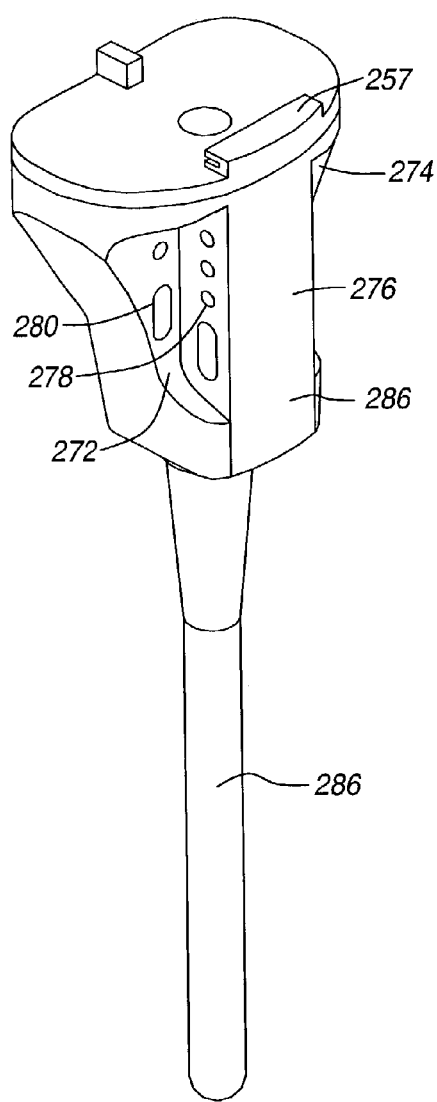
FIGS. 27–29 depict an alternate tibial component with integral soft tissue fixation mechanism.

As can be seen in FIGS. 25 and 27, the first and second apertures 278 and 280 can be circular or oval to facilitate the coupling of various types of soft tissue connecting mechanisms to the soft tissue fixation member 286. It is envisioned that other suture fixation mechanisms such as loops or retention flanges can be used.

Figure 29:
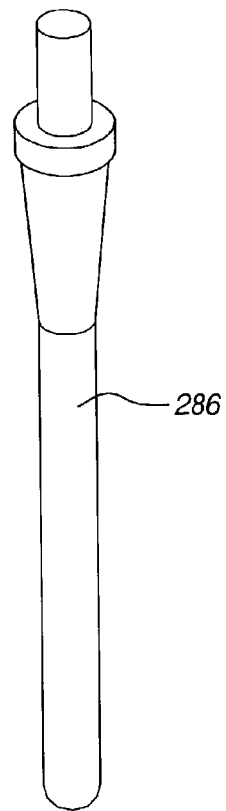
Figure 30:
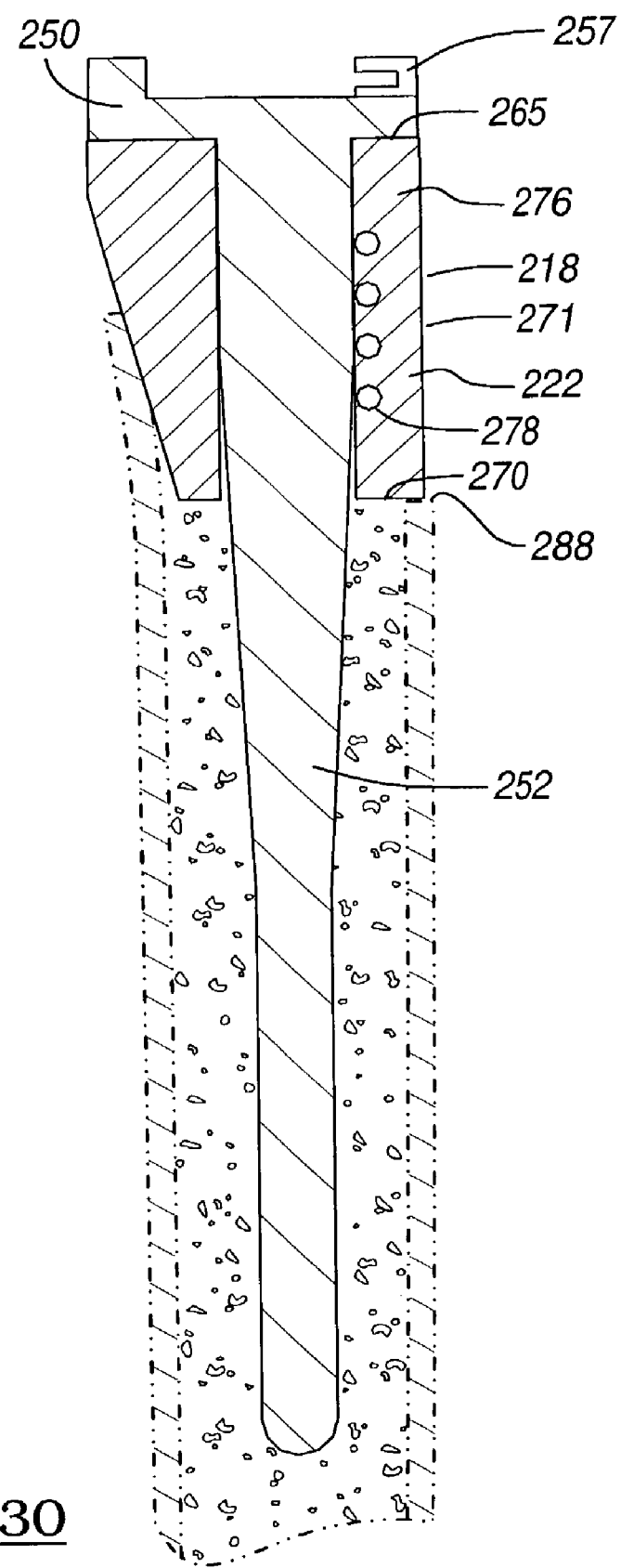
FIG. 30 represents a cross-section of the tibial component according to FIG. 18 being implanted into a resected tibia.

FIGS. 30–32 represent the implantation of the orthopedic implant 210 as shown in FIG. 17 into a resected tibia and femur. As can be seen in FIG. 29, the tibia 212 is resected forming a generally planar bearing surface 288. The soft tissue fixation mechanism 222 is disposed adjacent to this resected surface while the stem 252 is inserted into the longitudinal center of the tibia 212. While a fixed bearing 220 is shown, it should be understood that other prosthetic knee types are equally applicable such as a cruciate retaining, posterior stabilized, fully constrained with either fixed or mobile bearing or a hinged knee.

The fixed bearing 220 is located between the femoral component 216 and the tibial component 218. The fixed bearing 220 has a substantially planar inferior bearing surface 258 which is fixed relative to the tibial bearing surface 256, and further includes a first superior articulating or bearing surface 259 and a second superior fixed bearing surface 259a. The first bearing surface 259 articulates with the first bearing surface 226 of the condyle 221 and the second bearing surface 228 of the condyle 223 of the femoral component 216. Positioned between the first and second bearing surfaces 259 and 259a is a coupling portion 262 that is fixably positioned adjacent the fixation mechanism 257 on the tibial tray 250. The coupling portion 262 is defined by a substantially perpendicular peripheral aperture 266 which is operable to engage the fixation mechanism 257 by use of a locking pin 265. The fixed bearing 220 is preferably formed from a surgical grade, low friction, low wearing plastic, such as UHMWPE or other suitable material. Soft tissue is coupled to the soft tissue attachment mechanism 222 using sutures 290.

While the soft tissue attachment mechanism is shown throughout the application as a cylindrical tube disposed about a implant positioned within an intermedullary canal, it should be noted that the soft tissue fixation members can further take the form of a plate coupled to either a cylindrical or flat baseplate member. In this regard, the soft tissue fixation mechanisms can take the form of a plate member capable of accepting a suture or suture anchor. Additionally, the prosthetic need not be associated with a joint, e.g. an intercalary member.

Additionally, the soft tissue fixation mechanisms can be adjustably positioned on the prosthetic in one or more fixation areas. In this regard, multiple soft tissue fixation mechanisms can be located on multiple locations of a single implant. While the soft tissue fixation mechanisms is shown on a modular prosthetic, those skilled in the art will recognize that only the soft tissue fixation mechanisms need be modular and that the soft tissue fixation mechanisms can be fixed to any single piece prosthetic device. It is envisioned that a kit can be formed utilizing various sized prosthetic as well as various types and sizes of soft tissue coupling mechanisms.

The description of the invention is merely exemplary embodiments in the present invention. One skilled in the art would readily recognize from such discussion and from accompanying drawings and claims that various changes, modifications, variations may be made therein without the spirit and scope of the invention. For example, while the soft tissue fixation mechanisms are shown being coupled to a humeral, femoral, or tibial implant, the soft tissue fixation mechanism can equally be applied to other joint implants such as, but not limited to, knees and elbows, and for whole bone replacement.

Additionally, while the base member is shown being disposed outside of an intermedullary canal, it is possible to position at least a portion of the base member 32 within a bone structure. Further, while the fixation members are shown as transverse and longitudinal flanges, they can equally be positioned in any direction, or can take the form of a depression within the surface of the soft tissue fixation mechanism exterior.

What is claimed is:

1. A knee joint prosthesis for replacing an articulating knee portion of a femur and a tibia in an anatomy and being coupled to a portion of soft tissue that extends from a portion of the anatomy, said knee joint prosthesis comprising:
   a femoral component having an engagement member configured to be mated with a resected femur, said femoral component having a first femoral bearing surface and a second femoral bearing surface;
   a tibial component having a tibial bearing surface and defining an attachment region, wherein the attachment region defines a locking mechanism, and further wherein said attachment region defines a channel and a locking device including a flange;
   a bearing member having a first bearing surface operable to articulate with said first femoral bearing surface, a second bearing surface operable to articulate with said second femoral bearing surface, and a third bearing surface operable to engage said tibial bearing surface; and
   a soft tissue fixation member operable to be attached to said attachment region and to the soft tissue that extends from the portion of the anatomy.

2. The orthopedic implant according to claim 1 wherein the soft tissue fixation member defines an aperture operable to engage the soft tissue.

3. The knee joint prosthesis according to claim 1 wherein the flange is a tapered flange.

4. The knee joint prosthesis according to claim 1 wherein the attachment region defines a plurality of channels.

5. The knee joint prosthesis according to claim 1 wherein said knee joint prosthesis is selected from the group of a cruciate retaining joint, a posterior stabilized joint, a constrained joint with fixed bearing, a constrained joint with mobile bearing, and a hinged joint.

6. The knee joint prosthesis according to claim 1 further comprising a tapered stem coupled to said tibial component.

7. The knee joint prosthesis according to claim 1 further comprising a bone fixation member coupled to said tibial component.

8. The knee joint prosthesis according to claim 1, wherein said bearing member engages said tibial bearing surface in at least one of a substantially fixed manner or a mobile manner.

9. A knee joint prosthesis for replacing an articulating knee portion of a femur and a tibia in an anatomy and being coupled to a portion of soft tissue that extends from a portion of the anatomy, said knee joint prosthesis comprising:
   a femoral component having an engagement member configured to be mated with a resected femur, said femoral component having a first femoral bearing surface and a second femoral bearing surface;
   a tibial component having a tibial bearing surface and defining an attachment region, wherein the attachment region defines a locking mechanism;
   a bearing member having a first bearing surface operable to articulate with said first femoral bearing surface, a second bearing surface operable to articulate with said second femoral bearing surface, and a third bearing surface operable to engage said tibial bearing surface; and
   a soft tissue fixation member operable to be attached to said attachment region and to the soft tissue that extends from the portion of the anatomy, wherein the soft tissue fixation member comprises a flange defining a suture bore therethrough.

10. The knee joint prosthesis according to claim 9 wherein the flange defines a plurality of suture bores.

11. The knee joint prosthesis according to claim 9 wherein said bearing member engages said at least one tibial bearing surface in at least one of a substantially fixed manner or a mobile manner.

12. A knee joint prosthesis for replacing an articulating knee portion of a femur and a tibia in an anatomy and being coupled to a portion of soft tissue -that extends from a portion of the anatomy, said knee joint prosthesis comprising:
   a femoral component having an engagement member configured to be mated with a resected femur, said femoral component having a first femoral bearing surface and a second femoral bearing surface;

a tibial component having a tibial bearing surface and defining an attachment region;

a bearing member having a first bearing surface operable to articulate with said first femoral bearing surface, a second bearing surface operable to articulate with said second femoral bearing surface, and a third bearing surface operable to engage said tibial bearing surface; and a soft tissue fixation member operable to be attached to said attachment region and to the soft tissue that extends from the portion of the anatomy, wherein the fixation member is a flange defining a suture bore therethrough and wherein said suture bore includes a plurality of suture bores that are radially disposed about an exterior surface.

13. The knee joint prosthesis according to claim 12, wherein said soft tissue fixation member includes a locking mechanism.

14. A knee joint prosthesis for replacing an articulating knee portion of a tibia in an anatomy which interfaces with an articulating portion of a femur, said knee joint prosthesis comprising:

a tibial component having at least one tibial bearing surface and an attachment mechanism, wherein said attachment mechanism defines a taper, and further wherein said attachment mechanism defines a channel and wherein said soft tissue fixation member comprises a flange configured to mate with said channel;

a tapered stem coupled to said tibial component;

a bearing member having a first bearing surface operable to articulate with the femoral articulating portion and a second bearing surface operable to engage with said at least one tibial bearing surface; and a soft tissue fixation member operable to be attached to said attachment mechanism and to soft tissue, wherein the soft tissue extends from a portion of the anatomy.

15. The knee joint prosthesis according to claim 14 wherein said taper is a Morse taper.

16. The knee joint prosthesis according to claim 14 wherein said attachment mechanism defines a plurality of channels.

17. A knee joint prosthesis for replacing an articulating knee portion of a tibia in an anatomy which interfaces with an articulating portion of a femur, said knee joint prosthesis comprising:

a tibial component having at least one tibial bearing surface and an attachment mechanism, wherein said attachment mechanism defines a taper, and further wherein said soft tissue fixation member comprises a flange;

a tapered stem coupled to said tibial component;

a bearing member having a first bearing surface operable to articulate with the femoral articulating portion and a second bearing surface operable to engage with said at least one tibial bearing surface; and a soft tissue fixation member operable to be attached to said attachment mechanism and to soft tissue, wherein the soft tissue extends from a portion of the anatomy.

18. The knee joint prosthesis according to claim 17 wherein said flange is perpendicular to a central defining axis of said tibial component.

19. The knee joint prosthesis according to claim 17 wherein said soft tissue fixation member defines a soft tissue fixation hole.

20. The knee joint prosthesis according to claim 17 wherein said soft tissue fixation member defines a soft tissue fixation slot.

21. A knee joint prosthesis for replacing an articulating knee portion of a tibia in an anatomy which interfaces with an articulating portion of a femur, said knee joint prosthesis comprising:

a tibial component having at least one tibial bearing surface and an attachment mechanism;

a tapered stem coupled to said tibial component;

a bearing member having a first bearing surface operable to articulate with the femoral articulating surface and a second bearing surface operable to engage with said at least one tibial bearing surface; and a soft tissue fixation member operable to be attached to said attachment mechanism and to soft tissue, wherein the soft tissue extends from a portion of the anatomy and wherein said soft tissue fixation member is configured to be slidably disposed over said tapered stem.

22. The knee joint prosthesis according to claim 21 wherein said bearing member is one of a floating bearing or a fixed bearing.

23. A method for implanting an orthopedic knee prosthetic in an anatomy comprising:

selecting an appropriately sized knee prosthetic;

determining if soft tissue fixation to the knee prosthetic is necessary;

attaching a soft tissue fixation mechanism to the knee prosthetic, wherein attaching said soft tissue fixation mechanism to said knee prosthetic includes disposing said soft tissue fixation mechanism about said knee prosthetic;

implanting said knee prosthetic; and if determined necessary, interconnecting a soft tissue portion extending from a portion of the anatomy to a portion of the knee prosthesis.

24. The method according to claim 23 further comprising coupling soft tissue to the soft tissue fixation mechanism.

* * * * *